(12) United States Patent
Dykas et al.

(10) Patent No.: US 7,021,134 B2
(45) Date of Patent: Apr. 4, 2006

(54) MICROFLUIDIC ISOLATION MANIFOLD AND METHODS FOR MICROFLUIDIC ISOLATION

(75) Inventors: Thomas C. Dykas, Bellingham, WA (US); Michael L. Bailey, Concrete, WA (US); Nathaniel E. Nienhuis, Oak Harbor, WA (US)

(73) Assignee: Upchurch Scientific, Inc., Oak Harbor, WA (US)

( * ) Notice: Subject to any disclaimer, the term of this patent is extended or adjusted under 35 U.S.C. 154(b) by 0 days.

(21) Appl. No.: 10/795,588

(22) Filed: Mar. 8, 2004

(65) Prior Publication Data

US 2004/0261522 A1  Dec. 30, 2004

Related U.S. Application Data

(60) Provisional application No. 60/453,074, filed on Mar. 7, 2003.

(51) Int. Cl.
   *G01F 1/68* (2006.01)
   *G01F 15/14* (2006.01)

(52) U.S. Cl. ..................... 73/204.22; 73/273

(58) Field of Classification Search .. 73/202.5–204.27, 73/202
See application file for complete search history.

(56) References Cited

U.S. PATENT DOCUMENTS 4,735,094 A * 4/1988 Marsh ..................... 73/861.24
6,588,268 B1 * 7/2003 Yamagishi et al. ...... 73/204.26

\* cited by examiner

*Primary Examiner*—Harshad Patel
(74) *Attorney, Agent, or Firm*—Vinson & Elkins L.L.P.

(57) ABSTRACT

Apparatus and methods for isolating a component of a microfluidic analytical system are provided. An isolation manifold including a housing is used to isolate a sensitive component of a microfluidic analytical system from environmental noise and interference, such as mechanical vibrations and the like. The housing of the manifold includes an interior portion and a recess adapted to receive at least a portion the component to be isolated, such as a flow sensor. The housing has openings which allow for fluid communication through the housing to tubing used to connect the component to the analytical system. A potting agent can be used to help secure the component in place within the housing and to help minimize the potential for damage to the component.

24 Claims, 7 Drawing Sheets

MICROFLUIDIC ISOLATION MANIFOLD AND METHODS FOR MICROFLUIDIC ISOLATION

CLAIM OR PRIORITY

This application claims priority to U.S. Provisional Patent Application Ser. No. 60/453,074, filed Mar. 7, 2003, which is incorporated herein by reference.

FIELD OF INVENTION

This invention relates to fluidic connections useful in liquid chromatography and other analytical methods. More specifically, this invention relates to isolation manifold apparatus and methods of use that are useful in microfluidic chromatography and other analytical applications.

BACKGROUND

In many analytical applications such as liquid chromatography, the volumes of fluids and/or gasses are small. This is particularly true when liquid or gas chromatography is being used as an analytical method as opposed to a preparative method. Such conventional methods often use capillary columns and are sometimes referred to as capillary chromatography. In capillary chromatography, both gas phase and liquid phase, it is often desirable to minimize the internal volume of any and all components within the flow path of the sample stream, such as selection or injection valves, columns, filters, fittings, tubing, check valves, pressure regulators, detectors, and any sensors that may be used to characterize the conditions within the system. One reason for this control of volumes is that a component having a relatively large internal volume will contain a relatively large volume of fluid or gas. When a sample is introduced into such a component, the sample may be diluted, decreasing the resolution and sensitivity of the analytical method. Similar problems exist in connection with other conventional analytical applications, such as mass spectrometry and capillary flow electrophoresis.

Microfluidic analytical applications also involve small sample sizes. As used herein, sample volumes considered to involve microfluidic techniques can range from as low as only several picoliters or so, up to volumes of several milliliters or so. By comparison, more traditional LC techniques historically often involved samples of about one microliter to about 100 milliliters in volume. Thus, the microfluidic techniques and applications described herein involve volumes one or more orders of magnitude smaller in size than historic LC techniques. Microfluidic techniques can also be expressed as those involving flow rates of about 0.5 ml/minute, or less.

Another problem often encountered in microfluidic applications is the adverse effect(s) that environmental noise or interference may have on the equipment and system, thereby possibly affecting the analyses and test results. Such noise may come from a variety of sources, including environmental electric/electronic or magnetic radiation, mechanical vibrations, thermal changes, and the like. As sample sizes to be analyzed become smaller, and as the components of a liquid chromatography system (or other analytical system) become smaller, more sensitive and more delicate, the potential harmful effects of environmental noise on the system and its components, and their performance, become much greater.

Still another problem often encountered with microfluidic applications results from the fragile nature of conventional components. For example, fused silica tubing is often used for such applications, but is extremely delicate. Such tubing can be easily broken if scratched or struck. The fragile nature of such tubing and other components means that an operator using the same, such as by connecting or disconnecting the same to an analytical system, needs to pay greater time and attention to avoid such breakage.

SUMMARY OF THE INVENTION

The present invention solves potential problems caused by environmental interference or noise with respect to sensitive microfluidic components by the use of an apparatus for isolating selected components of the system in a manifold to shield such components from environmental noise and its related effects. The isolation manifold comprises a housing having at least two ends in which openings are provided for receiving tubing through which a sample can be introduced. The housing also has at least one interior seating area which is adapted to receive a component to be shielded from environmental noise and its effects. The openings of the housing are adapted to be connected to the flow path of an analytical system, such as an LC system, by way of removably and sealingly connecting tubing to each opening. The manifold housing comprises at least one recess adapted to receive and hold at least a portion of a component of a microfluidic analytical system. The interior seating area of the housing can be filled with a material for further isolating the component from environmental noise and interference.

It is an object of the invention to provide an apparatus and methods for isolating a sensitive component of an analytical system from environmental interference.

It is another object of the invention to provide an apparatus and methods for isolating a sensitive component in a microfluidic analytical system to shield it from environmental interference which could affect the performance of the component.

It is still another object of the invention to provide an apparatus and methods for shielding a sensitive component in a microfluidic analytical system from environmental noise that can be easily connected to and disconnected from the analytical system.

It is still another object of the invention to provide methods for isolating a sensitive component of a microfluidic analytical system from environmental interference by shielding the component from same in a manifold.

These and other objects of the invention will be apparent to those skilled in the art from the following detailed description.

DETAILED DESCRIPTION OF THE PREFERRED EMBODIMENT

The drawings and following discussion address a preferred embodiment of the isolation manifold of the present invention in detail. Although the description of the preferred embodiment of the isolation manifold is for use in combination with a microfluidic mass flow sensor in a liquid chromatography (LC) system, those skilled in the art will appreciate that the present invention is not so limited, and for example includes isolation manifolds adapted for use with other components of other microfluidic analytical systems. Other sensitive components of such systems include columns, vacuum degassers, pressure sensors, flow cells, service plasma resonance tubes, cuvets for flow cytometry, and cuvets for capillary flow electrophoresis. Although the following description is with reference to a liquid chromatography (LC) system, those skilled in the art will appreciate that other analytical systems and applications may be used with the invention, such as gas chromatography, mass spectrometry and capillary flow electrophoresis.

Figure 1:
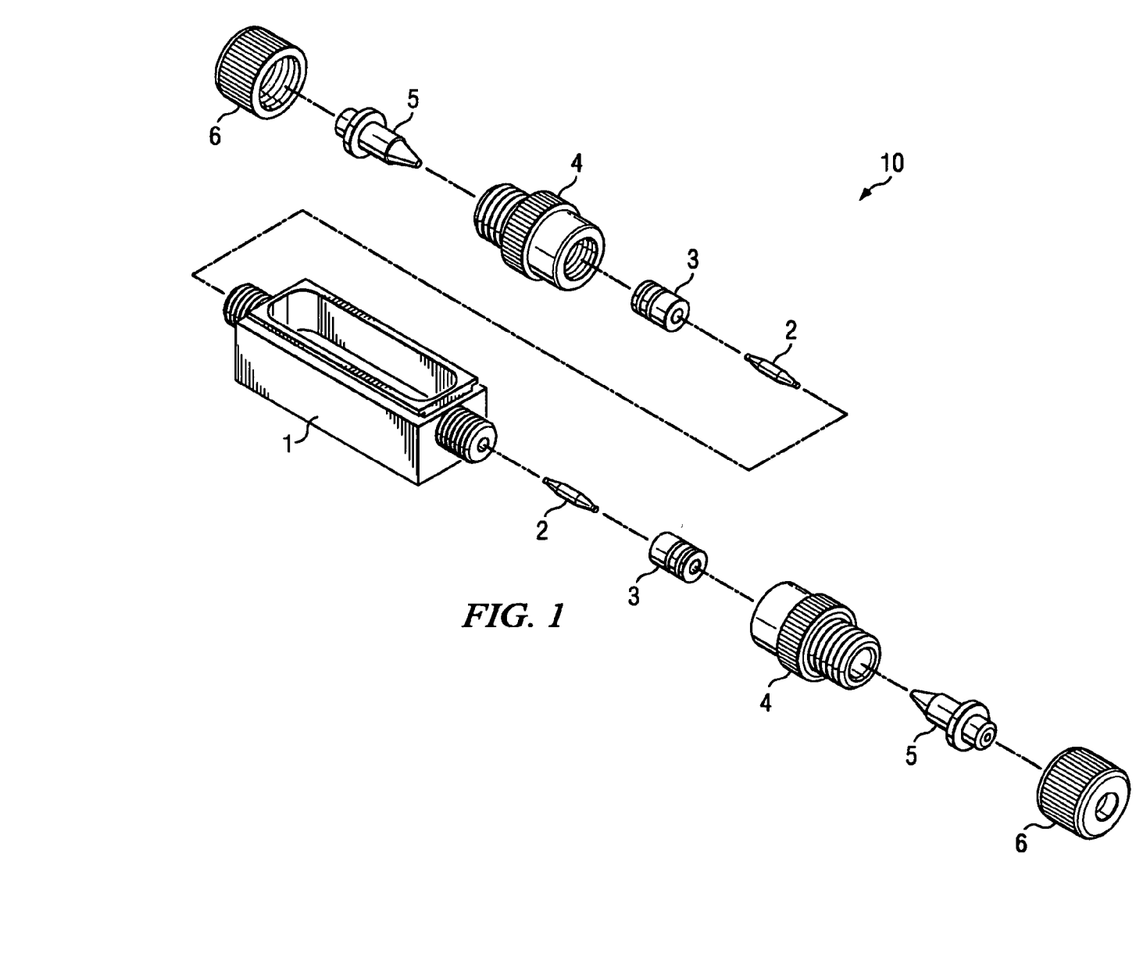
FIG. 1 is an exploded view of an embodiment of a manifold according to the present invention.

Referring to FIG. 1, an isolation manifold 10 is shown in an exploded view. As shown in FIG. 1, the manifold 10 comprises a housing 1 which has openings at two opposing ends. The manifold 10 also includes ferrules 2 adapted to sealingly fit into the openings of housing 1. The manifold 10 includes capsules 3 which have two ends, the first adapted to receive and sealingly fit one end of the ferrules 2, and the second adapted to sealingly fit into a first end of an adapter cap 4. The adapter caps 4 are, in turn, adapted to each have a second end which is adapted to receive and fit sealingly with a first end of a second ferrule 5. Finally, each of caps 6 have an end which is adapted to removably fit the second end of the adapter cap 4. As shown in FIG. 1, the caps 6 have internal threading which is adapted to allow the caps 6 to be screwed onto the second ends of the adapter caps 4, which have external threading. Similarly, the two opposing ends of the housing have externally threaded portions which are adapted to allow the first ends of the adapter caps 4 (which have internal threading) to be screwed into place. Although not shown in FIG. 1, those skilled in the art will appreciate that tubing can be used disposed within the open center portions of each of the caps 6, ferrules 5, adapter caps 4, and capsules 3 to allows for fluid communication via the tubing (not shown in FIG. 1) and the openings of the housing 1.

Figure 2:
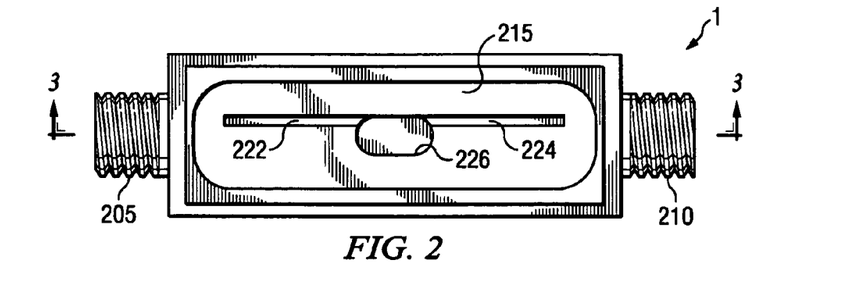
FIG. 2 is top view of the housing 1 of a manifold according to the present invention.

Referring now to FIG. 2, a top view of the housing 1 is shown. (The same numbers are used for the same components throughout the various figures, except with respect to alternative embodiments where noted.) As shown in FIG. 2, the housing 1 has two threaded end portions 205 and 210. As noted above, the end portions 205 and 210 are adapted to provide a removable connection between the housing 1 and adapter caps 4 (shown in FIG. 1). As shown in FIG. 2, the housing 1 also has an interior portion 215 open at the top side of the housing 1. The interior portion 215 is adapted to receive a component to be isolated from environmental interference. In a preferred embodiment of the invention, the interior portion 215 of the housing 1 is adapted to receive a flow sensor, such as that provided in the SLG liquid flow mass flow meter which is commercially available from Sensirion of Zurich, Switzerland. In a preferred embodiment of the invention, the housing 1 is made of a polymeric material, preferably polyetheretherketone (PEEK). In addition, the ferrules 2, capsules 3, adapter caps 4, ferrules 5, and caps 6 are made of PEEK in a preferred embodiment of the invention. We have found that PEEK provides certain advantages, including its low thermal conductivity and lack of electric conductivity. We believe that PEEK also helps dampen mechanical vibrations and other interference. Because PEEK is inert to biological specimens, such as blood, it also is suitable for use in applications where biocompatibility is of concern. Those skilled in the art will appreciate that other materials may be more appropriate depending on the specific application of the manifold 10.

Still referring to FIG. 2, the interior portion 215 also includes recesses 222, 224, and 226. In the preferred embodiment of the invention, recesses 222 and 224, respectively, are adapted to removably receive tubing (not shown in FIG. 2) connecting the internal openings 230 and 232 of the housing 1. (In the embodiment shown in FIG. 18 and discussed in detail below, the tubing 1830 is fused silica capillary tubing and extends through the openings of the ends of the housing 1100.) Recess 226 is adapted to receive a portion of a liquid flow mass sensor, such as the Sensirion sensor noted above. In a preferred embodiment a printed circuit board containing the liquid flow mass sensor at one end can be removably attached to the housing 1 so that the flow mass sensor is located within the recess 226 of the housing 1.

Figure 3:
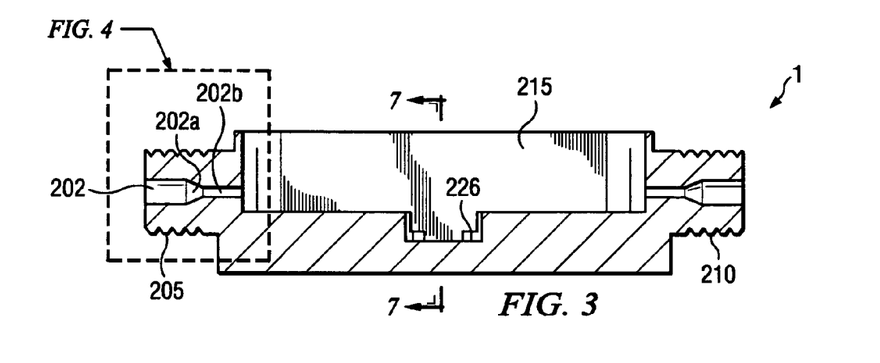
FIG. 3 is a sectional view of the housing 1 along line A—A of a manifold according to the present invention.

Referring now to FIG. 3, a sectional view of the housing 1 is shown. This view is taken along line A—A of FIG. 2. In FIG. 3, the interior portion 215 and the recess 226 are shown. In addition, FIG. 3 shows that each of the end portions of the housing 1 is adapted to receive one end of one of the ferrules 2. In addition, each of the ends of the housing 1 includes an opening 202 to allow fluid communication from the ends of the ferrules when attached to the end portions of the housing 1 (not shown) and the interior 215 of the housing 1. As shown in FIG. 3, the end portion 205 includes an interior chamber. The interior chamber includes a seating portion 202a as well as an opening 202b. As shown in FIG. 3, the seating portion 202a has a conical shape adapted to receive and provide a seal when a ferrule 2 (not shown in FIG. 3) is attached to the housing 1. The opening 202*b* allows fluid communication to the interior 215 of the housing.

Figure 4:
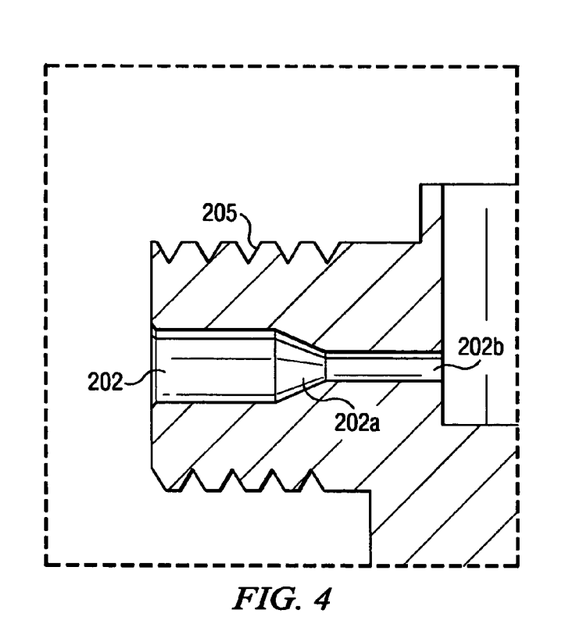
FIG. 4 is a detailed sectional view of one end portion of the housing of a manifold according to the present invention.

Referring now to FIG. 4, a detailed sectional view of one of the end portions of the housing 1 is shown. As shown in FIG. 4, the end portion 205 has a first opening 202 into which an end of the ferrule 2 can be placed when the housing 1 is connected to an LC system. In addition, the outside of the end portion 205 is threaded to allow an adapter cap 4 to be screwed onto at least of portion of the end 205 of the housing 1. When the adapter 4 is screwed onto the outside of the end portion 205 of the housing 1, the compression forces one end of the ferrule 2 into the conical seat 202*a* of the end portion 205, thus providing a sealed connection allowing for fluid communication between the interior 215 of the housing 1 and the LC system. The end portion 205 includes an opening 202*b* between the interior portion 215 of the housing and the outside of the housing beyond the end portion 205. The opening 202*b* has an internal diameter of about 0.027 inches, and is adapted to receive fused silica capillary tubing (not shown in FIG. 4) to extend therethrough, thus allowing fluid communication from outside the housing 1 through the end portion 205 and to the interior portion 215 of the housing 1.

Figure 5:
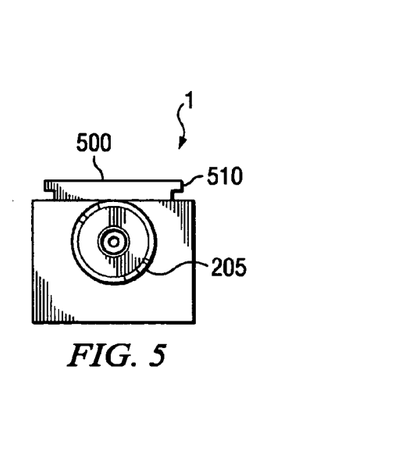
FIG. 5 is a side view of one end portion of the housing of a manifold according to the present invention.

Referring now to FIG. 5, an end view of the housing 1 is shown. In FIG. 5, the end portion 205 of the housing 1 is shown. As can be seen in FIG. 5, the top of the housing 1 includes a projecting portion 500 which has a lip 510. As shown in FIG. 5, the lip projects towards the outer sides of the housing 1 but does not extend all the way to the edge of the outer sides of the housing 1. The lip 510 is adapted to allow a housing (not shown in FIG. 5) containing a flow sensor (or other component to be isolated from environmental noise) to be removably attached to the top of the housing 1. Thus, those skilled in the art will appreciate that the a plastic housing for a flow sensor or other component (not shown in FIG. 5) to be used with the manifold 10 can be easily snapped into place on the top of the housing 1 and will be held in place by the lip 510.

Figure 6:
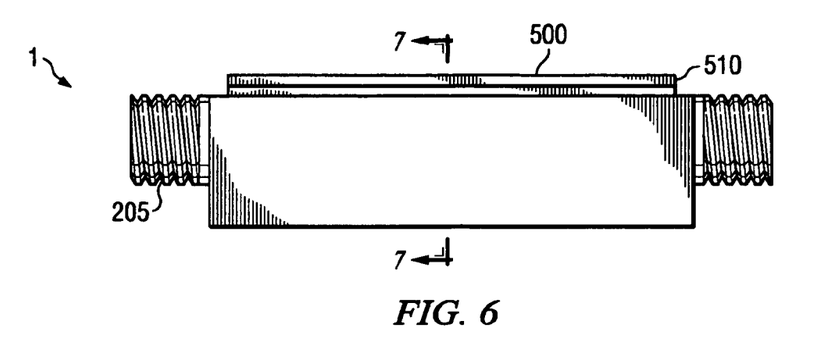
FIG. 6 is a side view of the housing of a manifold according to the present invention.

Referring now to FIG. 6, a side view of the housing 1 is shown. In FIG. 6, the lip 510 can be seen at the top of the housing 1, as can the threaded end portions of the housing 1.

Figure 7:
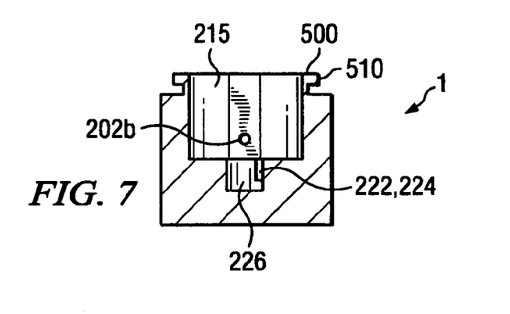
FIG. 7 is a sectional view along line C—C of the housing of a manifold according to the present invention.

In FIG. 7, a sectional view of the housing 1 along line C—C of FIG. 6 is provided. As shown in FIG. 7, the interior portion 215 is open to fluid communication with the LC system via the opening 202*a*. In addition, the lip 510 at the top of the housing 1 is shown. In addition, the recess 226 in the bottom of the interior portion 215 is shown. The relative size of recess 226 to recesses 222 and 224 is also shown in FIG. 7.

Figure 8:
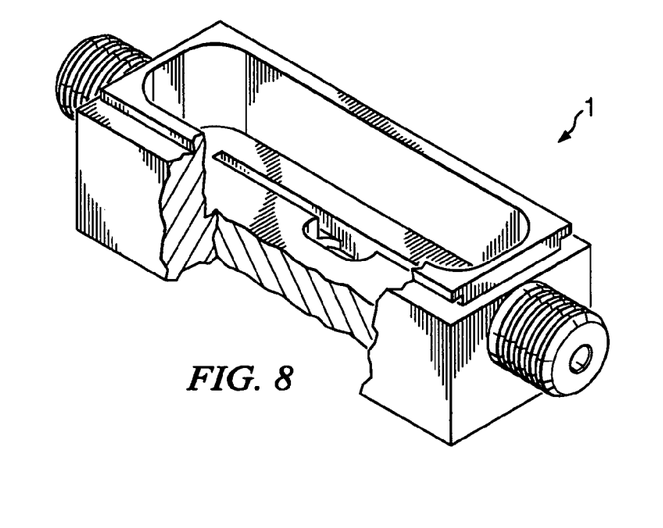
FIG. 8 is an isometric view of the housing of a manifold according to the present invention.

FIG. 8 illustrates an isometric view of the housing 1 of the manifold 10 and provides a view of the various features of the housing 1 noted above.

Figure 9:
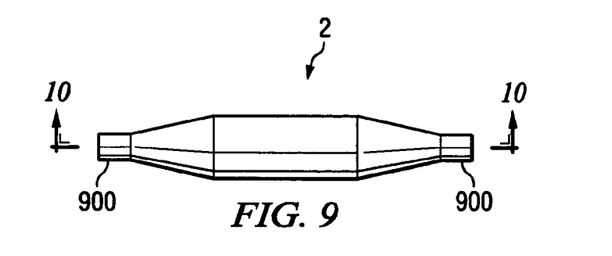
FIG. 9 is a side view of a ferrule adapted for use with the housing of a manifold according to the present invention.
Figure 10:
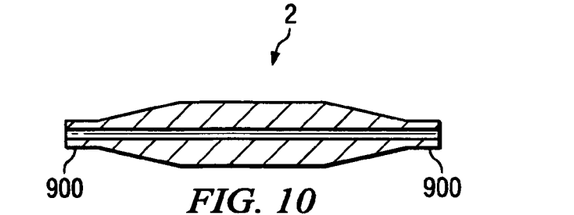
FIG. 10 is a sectional view along line A—A of FIG. 9 of the ferrule adapted for use with the housing of a manifold according to the present invention.

FIGS. 9 and 10 provide additional detail regarding the ferrules 2. As shown in FIGS. 9 and 10, each ferrule 2 has two end portions 900. In the preferred embodiment, the end portions 900 are adapted to sealingly fit into the seat 202*a* of the end portions 205 and 210 of the housing 1 and into a seat 33 of the capsule 3 (not shown), respectively. As shown in FIG. 10, the ferrule 2 has an opening therethrough to allow fluid communication between the ends of the ferrule 2. Those skilled in the art will appreciate that the use of ferrules 2 to be removably connected to the end portions 205 and 210 of the housing 1 will avoid the need to attach the tubing (not shown in FIG. 9 or 10) to a seat 202*a* at the end portions 205 and 210 of the housing 1. This allows an operator to removably connect the manifold 10 to tubing (not shown in FIG. 9 or 10) first and then connect such tubing (not shown in FIGS. 9 or 10) to an LC system. This also allows an operator to use various types of tubing outside the housing 1 to connect the component (not shown) within the housing 1 to the LC system. For example, an operator could use PEEK tubing (not shown) to connect an LC system to the end portions 205 and 210, even though the component to be located in the housing 1 may be connected to the openings 202*b* of the housing 1 by fused silica capillaries (not shown in FIG. 9 or 10). This allows an operator to more easily connect and disconnect the manifold 10 from the LC system because it minimizes the potential for breaking the fused silica capillaries within the housing (not shown in FIG. 9 or 10).

Figures 11, 15:
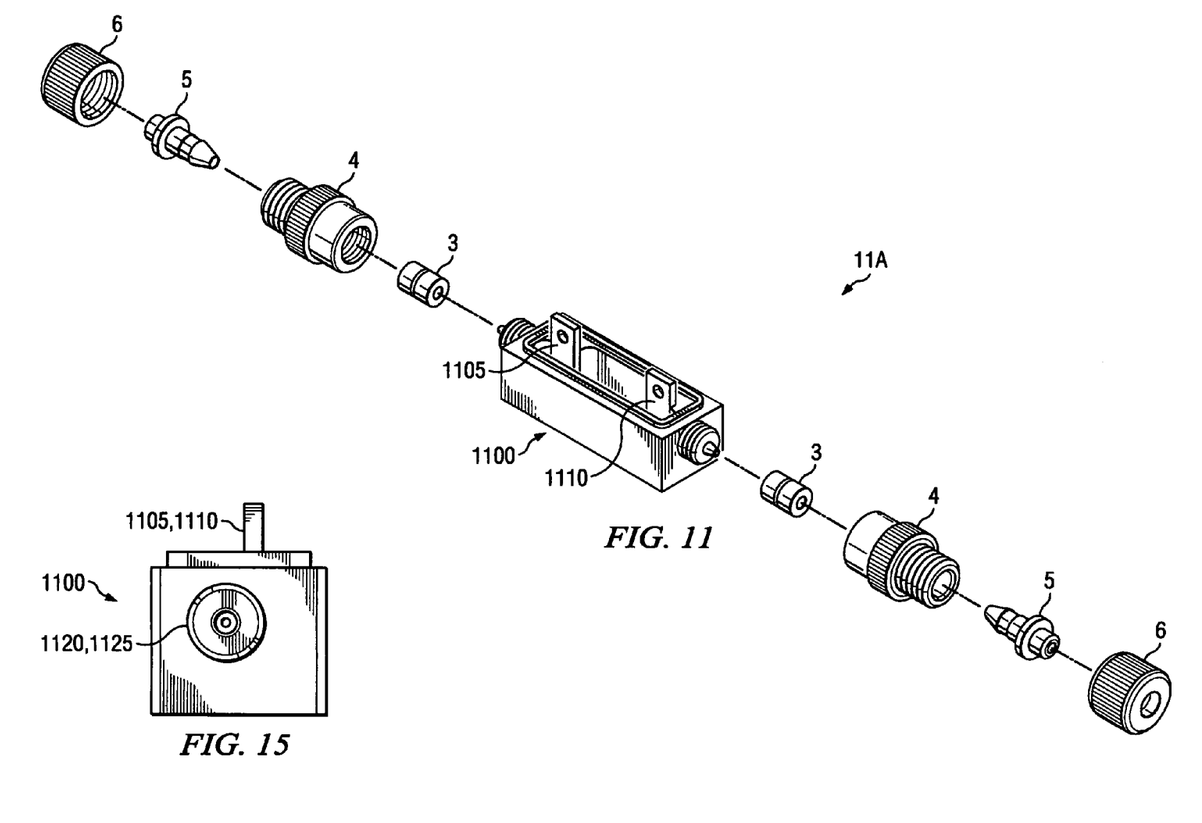
FIG. 11 is an exploded view of an alternative embodiment of a manifold according to the present invention.
FIG. 15 is an end view of one end of a housing of the alternative embodiment of the invention.

Referring now to FIG. 11, an alternative embodiment of a manifold 11A is shown in an exploded view. As shown in FIG. 11, the manifold 11A includes a housing 1100. The housing 1100 includes projecting portions 1105 and 1110. The projecting portions 1105 and 1110 are adapted to receive screws or other means for removably attaching a printed circuit board (not shown in FIG. 11) to the housing 1100. This allows the circuit board with a flow sensor attached thereto (not shown in FIG. 11) to be firmly and fixedly attached to the housing 1100.

Figure 12:
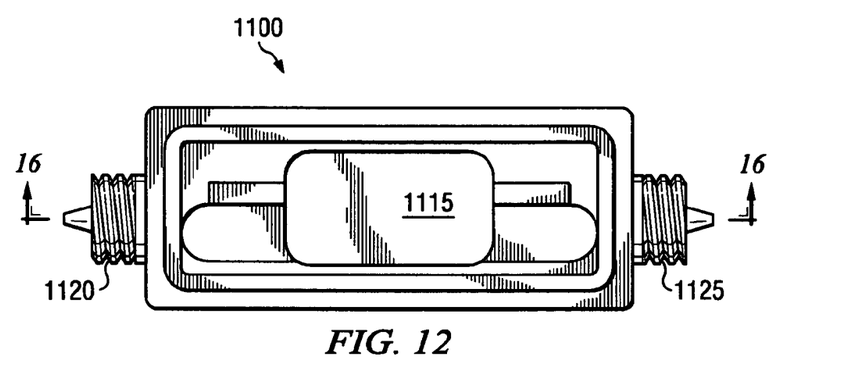
FIG. 12 is a top view of a housing of the alternative embodiment of a manifold according to the present invention.

Referring now to FIG. 12, a top view of the housing 1100 is shown. In FIG. 12, the housing 1100 includes end portions 1120 and 1125, discussed in more detail below. As with the housing 1 described above, the housing 1100 is preferably made of PEEK. The housing 1100 includes an interior portion 1115 which is open to the top side of the housing 1100.

Figure 13:
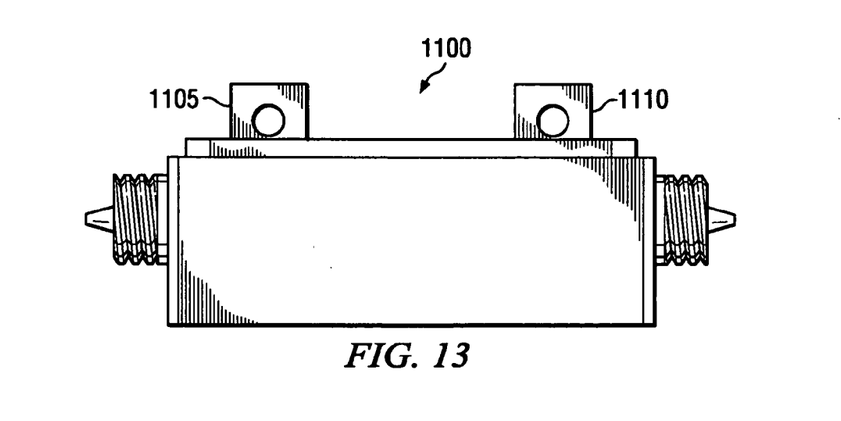
FIG. 13 is a side view of a housing of the alternative embodiment of a manifold according to the present invention.

In FIG. 13, a side view of the housing 1100 is provided. In this view, the projections 1105 and 1110 are clearly shown. Each of the projections 1105 and 1110 include openings therethrough for use in attaching a component or printed circuit board containing a component (not shown in FIG. 13) to the housing 1100. We prefer to attach a portion of a printed circuit board to which the flow sensor is attached (not shown in FIG. 13) to the housing 1100 by use of screws through the openings in projections 1105 and 1110. Those skilled in the art will appreciate that other means for attaching the printed circuit board (not shown in FIG. 13) to the housing 1100 could be used, such as by gluing the printed circuit board to the projections 1105 and 1110.

Figure 14:
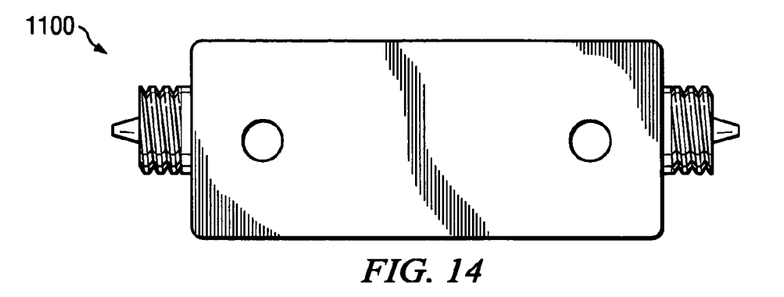
FIG. 14 is a bottom view of a housing of the alternative embodiment of a manifold according to the present invention.

FIG. 14 provides a view of the bottom of the housing 1100.

FIG. 15 provides an end view of one of the ends of the housing 1100. As shown in FIG. 15, each of the ends of the housing 100 includes one of end portions 1120, 1125, described in more detail below. In addition, the projections 1105, 1110 can be seen on the top side of the housing 1100.

Figure 16:
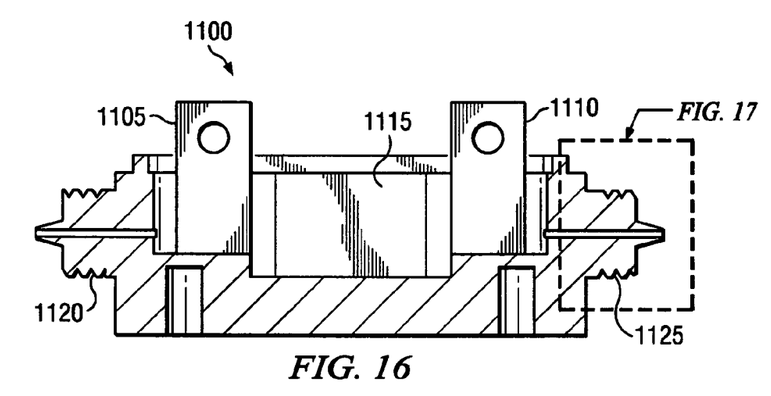
FIG. 16 is a sectional view along line A—A of FIG. 12 of a housing of the alternative embodiment of a manifold according to the present invention.
Figure 17:
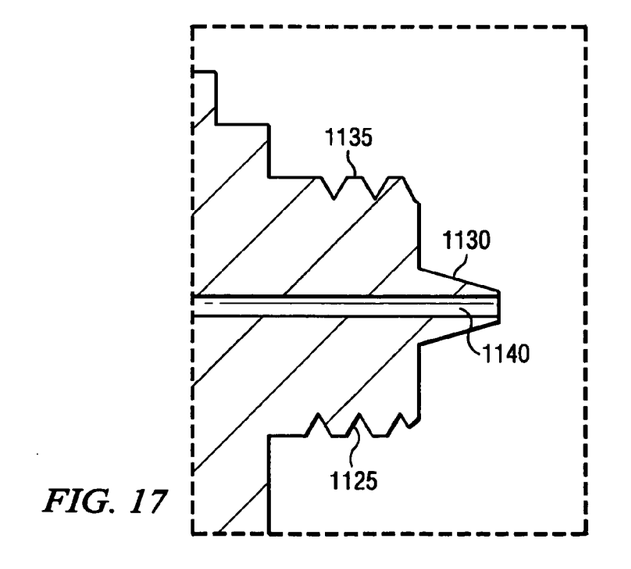
FIG. 17 is a detailed sectional view of one end of a housing of the alternative embodiment of a manifold according to the present invention.

Referring now to FIG. 16, a sectional view of the housing 1100 taken along line A—A of FIG. 12 is provided. In FIG. 16, it can be seen that the housing 1100 includes an interior portion 1115. The interior portion 1115 is open to the top side of the housing 1100. A detailed view of end portion 1125 is further provided in FIG. 17. As shown in FIG. 17, the end portion 1125 includes a tapered portion 1130, a threaded exterior portion 1135, and an opening therethrough 1140. The tapered portion 1130 is adapted to fit into a first end of the capsule 3 shown in FIG. 11. In addition, the threaded portion 1135 is adapted to receive and hold a first end of the adapter 4 shown in FIG. 11. When the adapter 4 of FIG. 11 is screwed onto the end portion 1135, the compression forces provide a seal between the tapered portion 1130 and the first end of the capsule 3 of FIG. 11. As shown in FIGS. 16 and 17, the opening 1140 allows fluid communication between the exterior of the housing 1100 and the interior portion 1115.

Figure 18:
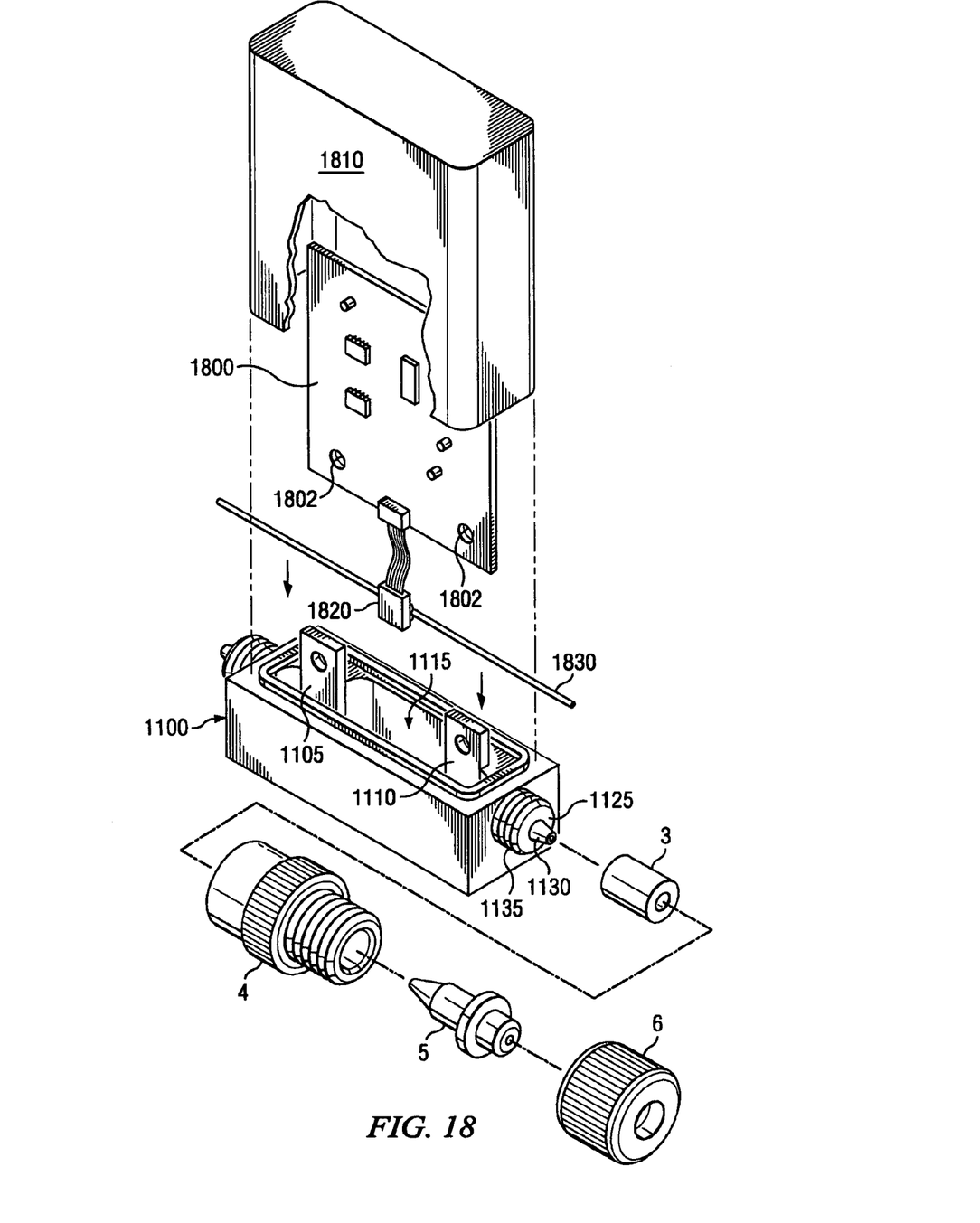
FIG. 18 is an exploded view of the use of a housing of an alternative embodiment of a manifold with a mass flow sensor connected to a printed circuit board.

Referring now to FIG. 18, an exploded view of the housing 1100, printed circuit board 1800, and cover 1810 is shown. As shown in FIG. 18, the housing 1100 is adapted to receive in its interior portion a portion of the printed circuit board 1800. Located at a bottom side of the printed circuit board 1800 is a mass flow sensor 1820. The mass flow sensor 1820 is bonded to fused silica tubing 1830. The printed circuit board 1800 includes two openings 1802 through which screws can be inserted for screwing the printed circuit board 1800 to the housing 1100 by way of projections 1105 and 1110. In practice, the tubing 1830 is bonded to the mass flow sensor 1820. The combination of the tubing 1830 and mass flow sensor 1820 is then placed in the interior 1115 of the housing 1100 from the open top side of the housing 1100. For best results, we prefer to have the tubing 1830 prepared so that a length of tubing about twice its diameter extends beyond the end of the tapered portion 1130 of the end portion 1125 of the housing 1100. The tubing 1830 can be disposed through the housing 1100, then the ends of the tubing 1830 extending from the ends of the housing 1100 can be cut to the desired length as noted. When a first end of the adapter 4 is screwed onto the threaded exterior portion 1135 of the housing 1100, the end of the tubing 1830 is held firmly and sealingly in place within the first end of the capsule 3 adapted to receive the tubing 1830 and tapered portion 1130. We have found that this approach results in essentially zero dead volume with respect to the fluid connections to and from the tubing 1830. However, it can also result in a bowing of the tubing 1830 within the housing 1100. We have found that the use of a potting agent (not shown) located in the housing 1100 around the tubing 1830 (such as in recesses 222, 224, and 226 as discussed above) helps prevent the tubing 1830 from breaking. Also shown in FIG. 18 is a cover 1810. The cover 1810 is adapted to fit over the printed circuit board 1800. The bottom side of the cover 1810 can be adapted to snugly fit over a lip on the top portion of the housing 1100 (not shown in FIG. 18, but shown as 510 in FIG. 5 in a different embodiment).

In still another embodiment, the interior 215 of the housing 1 can be filled with an adhesive or plastic material to fixedly attach the printed circuit board with the flow sensor (not shown in place with respect to the housing 1. Doing so helps minimize movement of the flow sensor relative to the housing 1. We prefer to use as a potting agent SLYGARD 184, which is commercially available from Dow Corning of Midland, Mich. This potting agent is silicone-based and helps keep the printed circuit board and flow sensor in place within the interior 215 of the housing 1. This potting agent also helps dampen mechanical vibrations and other environmental interference. We also believe that the use of this potting agent helps minimize the potential for damage to the fused silica tubing connecting the flow sensor to the openings 202b of the housing 1 from shocks, such as might result from being dropped or bumped by an operator, or which might result from sudden pressure drops or surges in the system when the flow sensor is connected to the LC system. As noted above, the use of a connection which seals when the adapter 4 is screwed onto the end of the housing 1100 may result in bowing of the tubing 1830. This bowing, in turn, may make the tubing 1830 more susceptible to damage. In practice, we prefer to provide the flow sensor and locate a portion of the flow sensor in the recess 226 of the housing 1, then connect the fused silica tubing to the openings 202b of the housing 1. Once a connection allowing fluid communication to and from the openings 202b and the flow sensor is accomplished, the potting agent can be disposed in the recess 226, as well as in recesses 222 and 224. Once the potting agent sets, it provides the advantages noted above.

As those skilled in the art will appreciate, the tubing and fittings described herein (with the exception of the housing 1,1100 and ferrules 2 and capsules 3 adapted to fit with housing 1,1100) can be those of a conventional type available from Upchurch Scientific, Inc. of Oak Harbor, Wash. Those skilled in the art will also appreciate that, although the manifold 10 described herein is of an embodiment for microfluidic applications, the invention may be used in other various analytical applications and may be used to isolate and shield various sensitive components of systems for analytical applications.

Those skilled in the art will appreciate that the foregoing description of the manifold 10 is of a preferred embodiment and of certain specific alternative embodiments, and that various changes, modifications and other variations and adaptations thereof may be made without departing from the scope and spirit of the invention as set forth in the claims. The specific embodiments, and the dimensions, materials, and the like are merely illustrative and are not intended to limit the scope of the invention, as set forth in the claims.

We claim:

1. An isolation manifold for microfluidic analysis applications, comprising:
   a housing having at least one inlet end and at least one outlet end, with each of the ends having an opening allowing fluid communication therethrough and having a plurality of projecting portions each having an opening therethrough adapted to receive tubing and each further comprising a threaded exterior diameter, and having an interior portion open to a top side of said housing, wherein the interior portion is adapted to receive and hold a flow sensor to isolate the sensor from external interference; and
   tubing located at least partially within the interior portion of said housing, wherein said tubing is sealingly connected to the projecting portions of the ends of said housing by sealing means comprising a plurality of ferrules each having a first end adapted to fit into at least a portion of the corresponding opening of said housing and having a second end adapted to fit into a first end of a corresponding opening of a capsule, wherein each said capsule has a second end adapted to fit into a first end of an adapter cap and wherein the first end of each said adapter cap comprises a threaded internal diameter adapted to engage the threaded exterior diameter of a corresponding projecting portion of said housing.

2. The manifold according to claim 1 wherein said housing comprises a polymeric material.

3. The manifold according to claim 1 wherein said housing comprises polyetheretherketone.

4. The manifold according to claim 1 wherein said housing consists of polyetheretherketone.

5. The manifold according to claim 1 wherein the internal diameter of each of the openings in the ends of said housing are no greater than about $15/1000$ of an inch.

6. The manifold according to claim 1 wherein the top portion of said housing comprises a lip adapted to removably hold a housing for a flow sensor.

7. The manifold according to claim 1 wherein the inlet end and the outlet end are at opposing ends of said housing.

8. The manifold according to claim 1 wherein the interior portion of said housing further comprises at least one recess adapted to receive a component of a flow sensor.

9. The manifold according to claim 8 where the component of the flow sensor is a microelectro-mechanical device.

10. An isolation manifold for isolating a sensitive component of a system for a microfluidic analytical application from environmental interference, comprising:
   a housing having first and second ends and having an interior portion open to a top side of said housing, wherein the first and second ends have openings adapted to receive tubing to allow fluid communication therethrough and openings having threaded portions, and wherein the top side of said housing comprises a projecting lip adapted to removably hold a housing for a component of a system for an analytical application, and wherein the interior portion of said housing comprises at least one recess adapted to receive at least a portion of a component for an analytical application; and
   means for sealingly connecting said housing to tubing to allow fluid communication to the system for an analytical application, wherein said sealing means comprises a plurality of ferrules, each having a first end having an exterior threaded portion adapted to sealingly engage at least a portion of the corresponding opening of said housing.

11. The manifold according to claim 10 wherein the component for an analytical application comprises one selected from the group consisting of a flow sensor, a column, a degasser, a flow cell, a service plasma resonance tube, a cuvet, a pressure transducer, a flow meter, a temperature sensor, a heat flux sensor, a displacement sensor, a load cell, a strain gauge, a conductivity sensor, a selective ion sensor, a pH sensor, a flow spectrophotometer, and a turbidity sensor.

12. The manifold according to claim 10 wherein the recess of the interior portion of said housing is adapted to receive at least a portion of a flow sensor meter.

13. The manifold according to claim 12 wherein said housing further comprises a plurality of projecting tabs on the top side of said housing, wherein each of said tabs are adapted to allow removable attachment of at least portions a printed circuit board to said tabs.

14. The manifold according to claim 13 wherein the interior portion of said housing further comprises a plurality of recesses, with at least one recess adapted to receive at least a portion of a tube with an opening therethrough to allow fluid communication through at least one of the openings of at least one of the ends of said housing to a flow sensor meter disposed in at least one other recess.

15. A method for isolating a component of a system for a microfluidic analytical application from environmental interference comprising the steps of:
   providing a housing having at least two ends with openings adapted to receive fused silica tubing extending through the housing and allowing fluid communication therethrough and having an interior portion which is open at a top side of said housing, and further having at least one recess adapted to receive at least one component of a system for a microfluidic analytical application having a portion adapted to fit in the at least one recess;
   locating a portion of the at least one component of the analytical system in the at least one recess of the housing; and
   locating at least a portion of the tubing adjacent at least a portion of the component located in the recess to allow the component to sense at least one property of a fluid in the tubing; and
   connecting the tubing through at least two ends of the housing to a portion of the system.

16. The method according to claim 15 wherein the at least one component comprises a flow sensor.

17. The method according to claim 16 wherein the flow sensor further comprises a printed circuit board.

18. The method according to claim 17 further comprising the step of securing at least a portion the printed circuit board to at least a portion of the housing.

19. The method according to claim 18 wherein said step of securing the portion of the circuit board to at least a portion of the housing comprises the step of providing a potting agent within the interior portion of the housing, wherein the agent at least partially fills a portion of the recess which is not otherwise occupied by the portion of the flow sensor located therein.

20. The method according to claim 19 wherein said potting agent comprises silicone.

21. The method according to claim 15 further comprising the step of disposing a potting agent within a portion of the interior of the housing.

22. The method according to claim 15 wherein the system for microfluidic analytical application comprises a liquid chromatography system.

23. The method according to claim 15 wherein the environmental interference comprises electric interference.

24. The method according to claim 15 wherein the environmental interference comprises mechanical vibrations.

* * * * *